(12) United States Patent
Couser

(10) Patent No.: US 10,993,636 B2
(45) Date of Patent: May 4, 2021

(54) SYSTEMS AND DEVICES FOR PROACTIVELY INFLUENCING BRAINWAVES

(71) Applicant: Daniel Joseph Couser, Glenmoore, PA (US)

(72) Inventor: Daniel Joseph Couser, Glenmoore, PA (US)

( * ) Notice: Subject to any disclaimer, the term of this patent is extended or adjusted under 35 U.S.C. 154(b) by 390 days.

(21) Appl. No.: 15/972,171

(22) Filed: May 6, 2018

(65) Prior Publication Data

US 2018/0317795 A1 Nov. 8, 2018

Related U.S. Application Data

(60) Provisional application No. 62/501,872, filed on May 5, 2017, provisional application No. 62/631,869, filed on Feb. 18, 2018.

(51) Int. Cl.

| *A61M 21/02* | (2006.01) |
|---|---|
| *A61B 5/0482* | (2006.01) |
| *A61B 5/048* | (2006.01) |
| *A61N 1/36* | (2006.01) |
| *A61B 5/00* | (2006.01) |
| *A61H 23/00* | (2006.01) |
| *A61B 5/04* | (2006.01) |
| *A61B 5/16* | (2006.01) |

(52) U.S. Cl.
CPC ............ *A61B 5/0482* (2013.01); *A61B 5/048* (2013.01); *A61B 5/6803* (2013.01); *A61B 5/6815* (2013.01); *A61B 5/7415* (2013.01); *A61H 23/00* (2013.01); *A61N 1/36096* (2013.01); *A61B 5/0022* (2013.01); *A61B 5/04012* (2013.01); *A61B 5/04014* (2013.01); *A61B 5/165* (2013.01); *A61B 5/742* (2013.01); *A61H 2230/105* (2013.01)

(58) Field of Classification Search
CPC .. A61M 2021/0027; A61M 2021/0044; A61M 21/00
See application file for complete search history.

(56) References Cited

U.S. PATENT DOCUMENTS

2010/0076253 A1\* 3/2010 Altman ................. A61M 21/00
600/28

\* cited by examiner

*Primary Examiner* — Christine H Matthews
(74) *Attorney, Agent, or Firm* — Offit Kurman, P.A.; Gregory A. Grissett

(57) ABSTRACT

An apparatus designed to induce brainwave synchronization in order to reduce or eliminate anxiety attacks, prevent stress and achieve desired brainwave states is disclosed. In operation, the device uses amplitude and frequency characteristics of stored .wav files containing isochronic or other tones to generate signals that are transmitted to the user through a variety of emission techniques including vibration, electrical, photic, and audial. The signals imparted to the user's cranium tend to be mimicked or followed such that the user's brainwave state is altered by the transmission of the desired signals. In various embodiments, the device and system may also possess bio-feedback and electroencephalogram capabilities. The device records metrics and usage data through a communications link with the user's smartphone, tablet or other device.

14 Claims, 14 Drawing Sheets

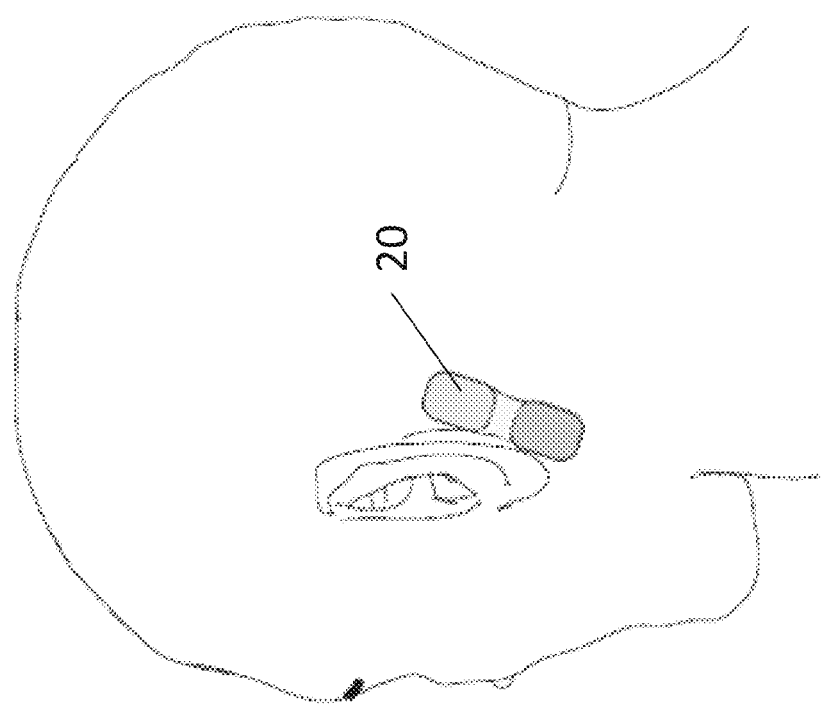

SYSTEMS AND DEVICES FOR PROACTIVELY INFLUENCING BRAINWAVES

CLAIM OF PRIORITY

This application claims the benefit of priority under 35 U.S.C. § 119(e) from U.S. Provisional Patent Application Ser. No. 62/501,872, filed on May 5, 2017, and Application Ser. No. 62/631,869, filed on Feb. 18, 2018, the benefit of priority of which for both applications is claimed hereby, and the contents of which are incorporated by reference herein in their entirety as if set forth in full.

FIELD OF THE INVENTION

The present invention generally relates to anxiety control devices and systems. In more particularity, embodiments of the devices and systems induce or influence brainwave synchronization by imparting stored waveform signals adjacent to or in proximity to the user's cranium. Through the induced synchronization of the user's brainwaves or brain state, embodiments of the devices and systems may be used to reduce or eliminate anxiety attacks, prevent stress and achieve desired brainwave states or conditions.

BACKGROUND DISCUSSION

Millions of individuals suffer from clinically diagnosed anxiety on a daily basis. There are countless other people who suffer and experience chronic and intense stress on a frequent basis, if not each day. While there are various medications to treat anxiety and chronic stress, there are no reliable, widely accepted non-pharmaceutical treatment options available to sufferers, that are able to effectively prevent an anxiety attack, or stop an attack while it is happening.

When an anxiety attack occurs, the body typically reacts, in an involuntary fashion, by instituting a "fight or flight" condition or response. This condition or response is usually accompanied by an, often overwhelming, sense of fear or dread, that generally has no immediate or future threat directly posed to the individual. Health and medical counselors generally advise individuals who experience such attacks to use controlled breathing and other grounding techniques as a means to help control or subdue such an anxiety attack. Unfortunately, it is extremely difficult for an individual experiencing an anxiety attack to subdue the symptoms simply through breathing techniques, especially when the effects of a fight or flight response are, involuntarily and acutely manifested with both physical and mental characteristics.

When elevated anxiety or high stress levels commence, it is known that the person's brain emits higher levels of beta waves while also emitting decreased levels of alpha and theta waves. These high anxiety brain wave patterns (elevated and dominant beta waves) are associated with rapid and frenzied thoughts within the brain. It has been postulated that if an effective means existed for controlling higher levels of beta waves while also encouraging higher levels of alpha and theta waves, such a means, device or system could directly and substantively benefit those who experience anxiety attacks and uncontrolled high stress levels.

Several studies have been undertaken and positively show that one way to address the problem of controlling an anxiety attack is through a form of brainwave influencing or brain state induced synchronization. Such studies have shown that a subject's brain tends to follow or adjust to match certain frequencies that are imparted to or emitted to the subject's skull or cranium. More particularly, in a 2007 study, cortical stimulation with repetitive frequencies of 1 to 8 Hz was shown to increase phase synchronization in all EEG frequency bands (Will and Berg, 2007). Additionally, a further study evaluated treatment for cortisol induced anxiety in mice through use of rhythmical flickering photic stimulation at alpha frequencies from 9 to 11 Hz. This latter study showed improved performance on various behavioral tasks assessing anxiety, locomotor activity, social interaction, and despair (Kim, et al., 2016).

In view of these studies and the resulting data, the inventive device has been designed and is being tested to provide a new and innovative way to quickly alleviate symptoms of and stop anxiety attacks by proactively influencing brainwave activity through a variety of stimulation methods. In a primary embodiment of the device, periodic stimuli, or frequency waves, are used to synchronize the user's brainwaves to the frequency of the tones being transmitted. One example of such frequency waves includes isochronic tones or wave forms. In alternative embodiments, in addition to emitting periodic tones to the user, the performance of the device may be enhanced by using additional or alternative stimuli such as photic or audial.

SUMMARY OF THE INVENTION

The present invention overcomes the disadvantages of the prior art and fulfills the needs described above by providing devices and systems that allow users to discretely and directly reduce or alleviate anxiety attacks through proactive influencing of brainwave activity.

The inventive device induces brainwave synchronization and eliminates or reduces the effects of an anxiety attack. In certain desired embodiments, the device uses isochronic tones to induce a frequency following response in the brain, which in turn synchronizes the user's brainwaves to the frequency of the tones. In other aspects, the device also provides the user with an associated physical vibration to focus on and act as an anchor as part of the mechanism to control the anxiety attack.

A preferred embodiment of the invention is a device for influencing brainwaves and brain states, comprising (a) a housing conformably placeable upon the outer surface of an individual's skull; (b) at least one frequency transmitting element housed within said housing; (c) a switch to actuate said at least one frequency transmitting element; (d) a rechargeable power source housed within said housing; (e) a computer processor housed within said housing; (f) read only memory (ROM) coupled to said computer processor to store at least one .wav files; and (g) at least one wave form data file stored within said ROM as a .wav file; wherein when said switch is actuated, said computer processor reads said at least one wave form data file stored as a .wav file in said ROM, and said computer processor then drives said at least one frequency transmitting element to match said at least one wave form data file, imparting a signal to an individual's skull that matches characteristics of said at least one wave form data file.

Another embodiment of the invention is a device for influencing brainwaves and brain states, comprising (a) a housing conformably placeable upon the outer surface of an individual's skull; (b) at least one frequency transmitting element housed within said housing; (c) a switch to actuate said at least one frequency transmitting element; (d) a rechargeable power source housed within said housing; (e)

a computer processor housed within said housing; (f) read only memory (ROM) coupled to said computer processor to store at least one .wav files; and (g) at least one wave form data file stored within said ROM as a .wav file; wherein when said switch is actuated, said computer processor reads said at least one wave form data file stored as a .wav file in said ROM, and said computer processor then drives said at least one frequency transmitting element to match said at least one wave form data file, imparting a signal to an individual's skull that matches characteristics of said at least one wave form data file, wherein the wave form data file is an isochronic wave pattern.

Still a further embodiment of the invention is a system for influencing device for influencing brainwaves and brain states, comprising (a) a housing conformably placeable upon the outer surface of an individual's skull; (b) at least one frequency transmitting element housed within said housing; (c) a switch to actuate said at least one frequency transmitting element, said switch located within said housing; (d) a rechargeable power source housed within said housing; (e) a computer processor housed within said housing; (f) read only memory (ROM) coupled with said computer processor to store a plurality of .wav files; (g) a plurality of wave form data files stored within said ROM as .wav files; (h) at least one sensor to record at least one physiological metric of a user; (i) a data transmitter incorporated into said housing to transmit data received from said at least one sensor; (j) at least one remote device to receive data transmitted from said data transmitter; wherein when said switch is actuated, said computer processor reads said wave form data files stored as .wav files in said ROM, and said computer drives said at least one frequency transmitting element at a frequency matching at least one frequency of said wave form data files, whereby said frequency transmitting element imparts said at least one frequency to the outer surface of the user's skull.

Another embodiment of the invention is a system for influencing device for influencing brainwaves and brain states, comprising (a) a housing conformably placeable upon the outer surface of an individual's skull; (b) at least one frequency transmitting element housed within said housing; (c) a switch to actuate said at least one frequency transmitting element, said switch located within said housing; (d) a rechargeable power source housed within said housing; (e) a computer processor housed within said housing; (f) read only memory (ROM) coupled with said computer processor to store a plurality of .wav files; (g) a plurality of wave form data files stored within said ROM as .wav files; (h) at least one sensor to record at least one physiological metric of a user; (i) a data transmitter incorporated into said housing to transmit data received from said at least one sensor; (j) at least one remote device to receive data transmitted from said data transmitter; wherein when said switch is actuated, said computer processor reads said wave form data files stored as .wav files in said ROM, and said computer drives said at least one frequency transmitting element at a frequency matching at least one frequency of said wave form data files, whereby said frequency transmitting element imparts said at least one frequency to the outer surface of the user's skull, wherein the wave form data files include an isochronic wave pattern.

The inventive device and system allows individuals to substantially reduce or eliminate anxiety attacks, subdue the "fight or flight" response, and achieve other desired brain wave states. The device may also be effectively used during high stress situations that require precise, clear, and rapid critical thinking, such as, by way of example, law enforcement, commercial and military aviation personnel, professional athletes, and medical personnel. The device is also able to alleviate symptoms of many conditions by using frequency tone and signal stimulation through various methods including vibrational, electrical, photic, audial and other related methods. The device in different embodiments can emit the signal to the user in different ways. In various embodiments, the device may also incorporate bio-feedback and electroencephalogram capabilities.

BRIEF DESCRIPTION OF THE DRAWINGS

For the purposes of illustrating the invention, the attached drawings show certain aspects and embodiments that are presently preferred. However, it should be understood that the invention is not limited to the precise configuration and particular components or system elements as shown in the accompanying drawings, but rather is further disclosed and claimed according to the attached claims.

FIG. 3 illustrates an exemplary embodiment of the device as applied or placed on a user.

DETAILED DESCRIPTION OF EXEMPLARY EMBODIMENTS

Figure 1:
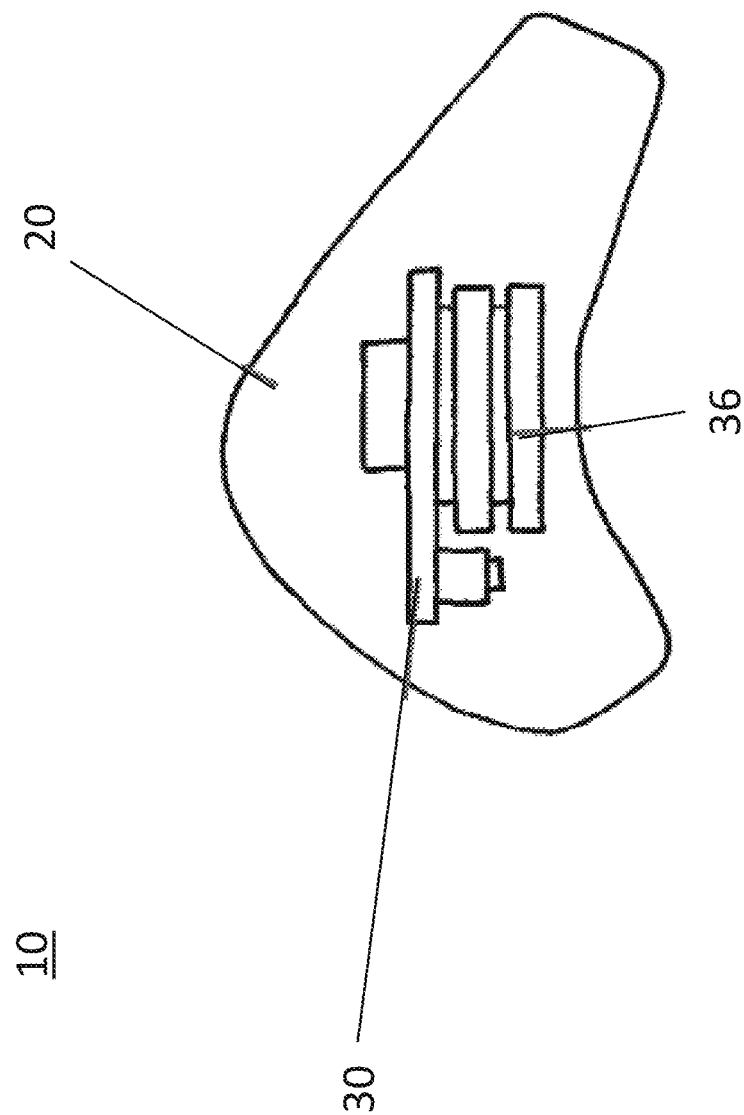
FIG. 1 shows an exemplary embodiment of the device from a side view illustrating the primary internal components of the device.

The present invention seeks to address and resolve the problems experienced by individuals suffering from involuntary anxiety attacks and involuntary elevated stress levels. Embodiments of the present invention allow users to discretely control and potentially alleviate involuntary anxiety attacks and high stress states.

At its core, the inventive system and device generates periodic stimuli that is imparted to users in order to encourage synchronization of the users' brainwaves to mimic the frequency of the desired periodic stimuli. The inventive system uses frequency waves, including by way of one example, isochronic tones, as a baseline or reference to which the user's brainwaves are encourage to synchronization or follow. In the form of isochronic tones, such wave patterns are pulses of a single tone emitted in equal intervals, creating a pulsating loop at a specific frequency. Depending on the frequency of the tones, a range of brainwave states can be achieved, resulting in various beneficial effects.

As illustrated in FIGS. 1 through 4D, the primary components of certain embodiments of the anxiety control device 10 include a housing 20 and a frequency transmitting element 30, such as a transducer, a tactile transduce, or a haptic element. Additional components used to operate and drive the anxiety control device 10 include a printed circuit board ("PCB") 35 that houses a microcontroller 36 and associated memory 37 on the PCB 35. The memory 37 is communicatively connected to, or embedded within the microcontroller 36, and to a transmitter/receiver 38 or transceiver components.

In operation, the anxiety control device 10 reads the amplitude and frequency of specific waveform signals 70 stored or recorded, as .wav files 71 in the microcontroller memory 37. The device 10 then transmits or imparts a form of the waveform signal 70 to the user through the frequency transmitting element 30. The frequency transmitting element 30 may use one or more of a variety of emission techniques including vibration, electrical, photic, and audial.

Signals 70 are imparted adjacent to or in the proximity of the user's brain such that the user's brain state or brain waves tend to follow those signals, thereby achieving altered brain states using a variety of device embodiments and signals. The device 10 is also designed to record various physiological and device metrics, as well as related usage data, as such data is collected through a wireless or wired system that communicates between the user's smartphone, tablet or device, a database and the brain state influencing device 10.

In various embodiments, the device 10 and system have the capability to use a wide variety of stimulation methods including vibration (for example tactile transmission, such as by a tactile transducer or bass shaker) and other similar methods. Additionally, the device 10 can be configured to use electrical, photic and/or audio stimulation to achieve the desired brainwave synchronization. In further embodiments, the system and device 10 may be outfitted to incorporate biofeedback and electroencephalogram capabilities to allow for the reading or recording of the user's brainwaves. Through such reading of brainwaves, the system 10 may be able to be adjusted, including by altering the imparted tone or transmission frequencies to achieve desired results.

Signals imparted to the brain such that the brain tends to follow those signals or change brain states can be achieved through a variety of device embodiments and signals. In a primary embodiment of the device 10, the user places the device transmitting element 30 behind his or her ear, at the base of the skull. A user can then activate the device 10 when they are experiencing increasing levels of stress, during an anxiety attack, or whenever they feel the need for an immediate clear mind. The individual simply places the device 10 at or on the instructed location, turns the device on, and his or her brain state will quickly react to synchronize the user's brainwaves to the frequency of the imparted periodic frequency tones. In other embodiments, the performance of the device 10 can be enhanced through various stimulation or emission methods, and/or various frequency imparting locations on the user.

Figure 4A:
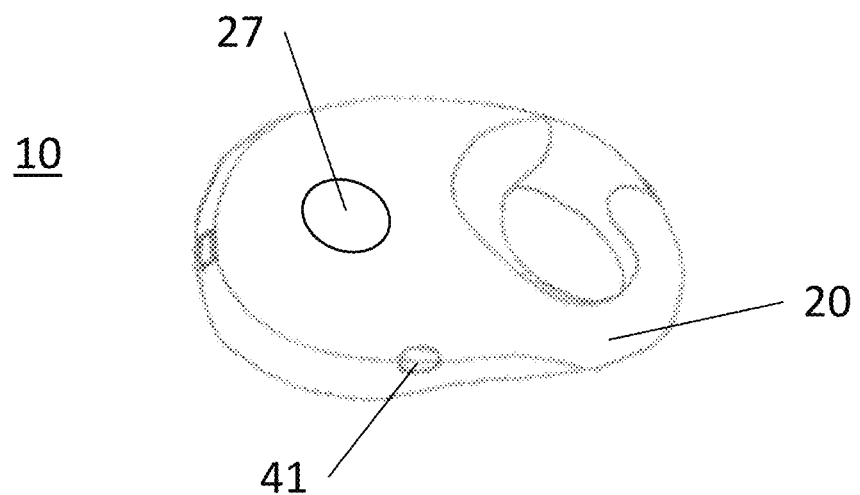
FIG. 4A shows a perspective view of an exemplary embodiment of the device configured as a pliable handheld unit.
Figure 4B:
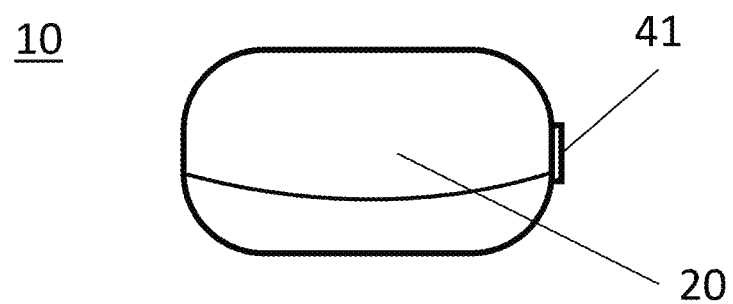
FIG. 4B shows a side view of an exemplary embodiment of the device configured as a pliable handheld unit.
Figure 4C:
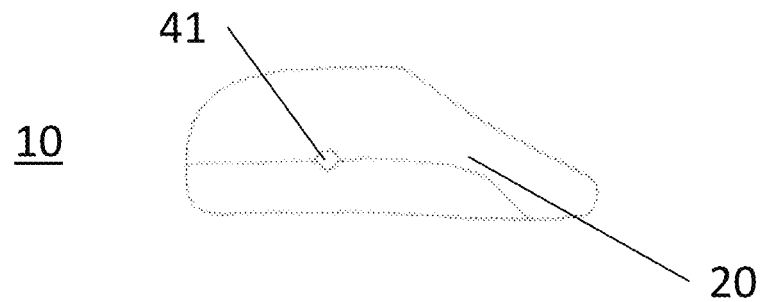
FIG. 4C shows another side view of an exemplary embodiment of the device configured as a pliable handheld unit.
Figure 4D:
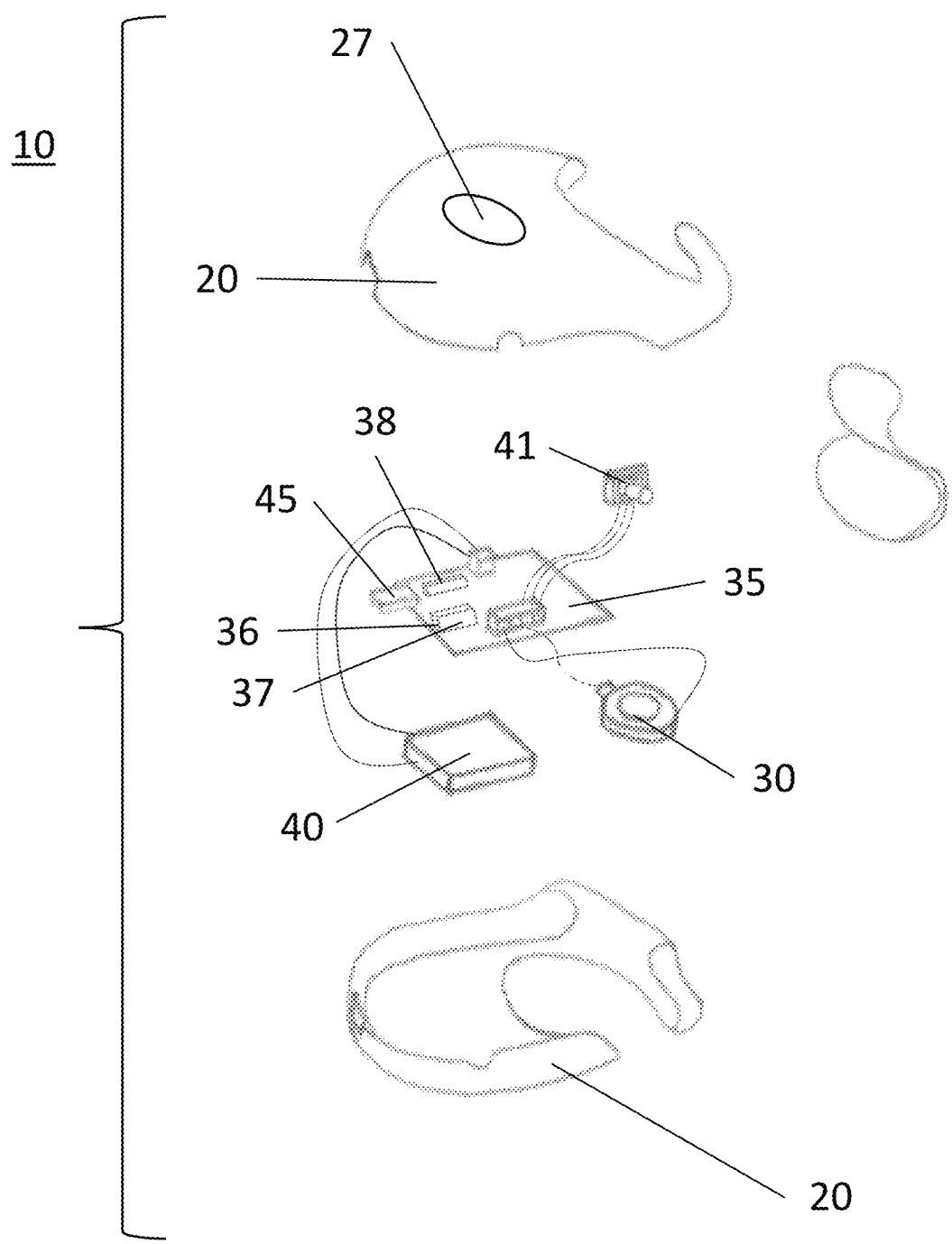
FIG. 4D shows a perspective view of an exemplary embodiment of the device configured as a pliable handheld unit in an exploded view illustrating the internal circuit elements and housing components.

As shown in FIGS. 1 through 4D, in particular FIG. 4D, examples of the device 10 include a printed circuit board 35 containing a microcontroller 36, associated memory 37, and a transmitter/receiver component 38. The printed circuit board (PCB) memory 37 stores a .wav file containing the frequency waves, or isochronic tones. The microcontroller 36 on the printed circuit board 35 reads the .wav file and sends a signal to the stimulation node 30 to emit the desired type of stimulation depending on the configuration, which in turn transmits the isochronic tones to the user.

The exemplary embodiment shown in FIGS. 4A and 4D further illustrates an opening 27 within the housing 20 that allows for direct contact between the stimulation node 30 and the user's skin. Such direct contact provides the most effective means of imparting the desired frequency signal to the user. In alternative embodiments (not shown), the housing 20 may not include an opening 27, but instead may have a thinner section proximate to the stimulation 30, or may have a thin, flexible material that covers the opening 27 but still allows for the frequency signal to be effectively transmitted to the user's cranium.

The method of stimulation can be changed depending on the configuration to impart one or more of vibration, electrical, photic and audial to influence brain states. As stated above, the device in different embodiments can emit the signal in different ways and with different signals.

In a further embodiment, the device 10 may also include a transmitter/receiver component 38 capable of transmitting data gathered by the device 10 to a remote database. This transmitter/receiver component 38 will record when the device is turned on, the duration of use, as well as other metrics or factors to record trends and patterns. The user will be able to download an external application on a smartphone, tablet or visit a website to view the recorded data and metrics.

The device 10, as illustrated in FIG. 4D, may be powered by a rechargeable and/or a removable battery source 40, and may have a recharging port 45. The device 10 in different embodiments may also have electroencephalogram (EEG) technology that will read the user's brainwaves. Based on these EEG readings, the device 10 can either send a notification to the user's phone when certain brainwave patterns are sensed, or automatically activate the device 10 to subdue unwanted brain states preemptively. The device 10 in certain embodiments can use a variety of equipment to measure brainwaves, as well as other physiological metrics, including sweat output, muscle tension, respiration rate, and heart rate.

Figure 2:
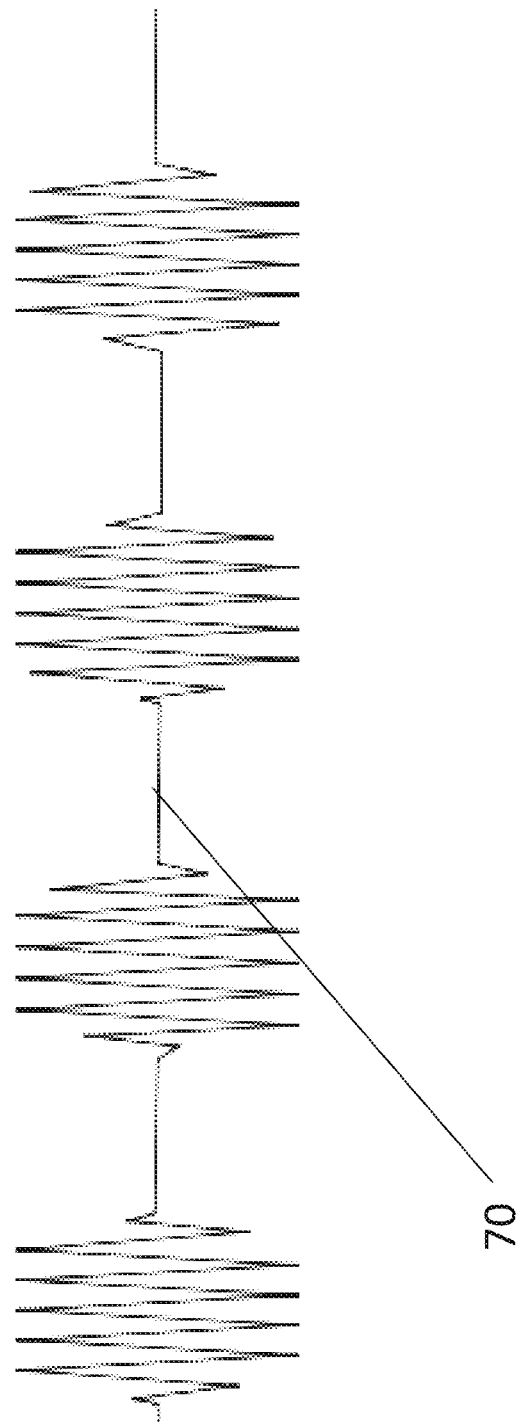
FIG. 2 shows an example of an isochronic tone signal.

FIG. 2 shows an illustrative example of an isochronic signal. The tone can be emitted at a range of frequencies to achieve different effects. For example, low frequency ranges such as theta waves, in the range of 4-8 Hz, to higher frequency ranges such as beta waves, in the range of 12-40 Hz. Signals imparted to the brain such that the brain tends to follow those signals or change brain states can be achieved through a variety of device embodiments and signals. While FIG. 2 shows and illustrates an isochronic signal with two dominant frequencies and one primary amplitude, alternative signal patterns may be stored within device 10 that have a plurality of or varying frequencies and a plurality of amplitudes.

As shown in FIG. 3, the device 10 can be placed behind the ear at the base of the skull to allow the vibrations to transmit directly through bone conduction. The device 10 can also be placed on other parts of the skull as long as the periodic frequency tones are being properly imparted to and decoded by the user's brain.

The individual is able to place and maintain the device 10 firmly in contact with his or her skull with various orientations through the unique design. When using vibrations and with the device 10 placed behind the ear (or on the skull), the vibrations bypass the eardrum and are signals are imparted directly to the cochlea. This will allow users to not only feel the vibrations, but also audibly hear the signals. In such a configuration, the individual can block the ear canal of his or her respective ear that the device is behind, which will create an intense and immersive audible effect. The device can emit isochronic tones, audibly and palpably, thereby increasing the effectiveness of inducing brainwave synchronization.

As also shown in FIGS. 3 and 10 through 16, the device 10 can be extremely compact and portable. Such a compact configuration allows users to operate and use the device discreetly. Often times, anxiety attacks and intense episodes of stress do not occur in the comfort of an individual's home, but rather at work, public or social events and other various settings where the individual is not alone and comfortable. An individual will be able to readily carry the device 10 in their pocket or any type of bag. This allows users to address the need to counter an anxiety attacks and de-escalate stress wherever they may be, and not having to worry about being able to address an involuntary anxiety and high stress attack.

Figure 5:
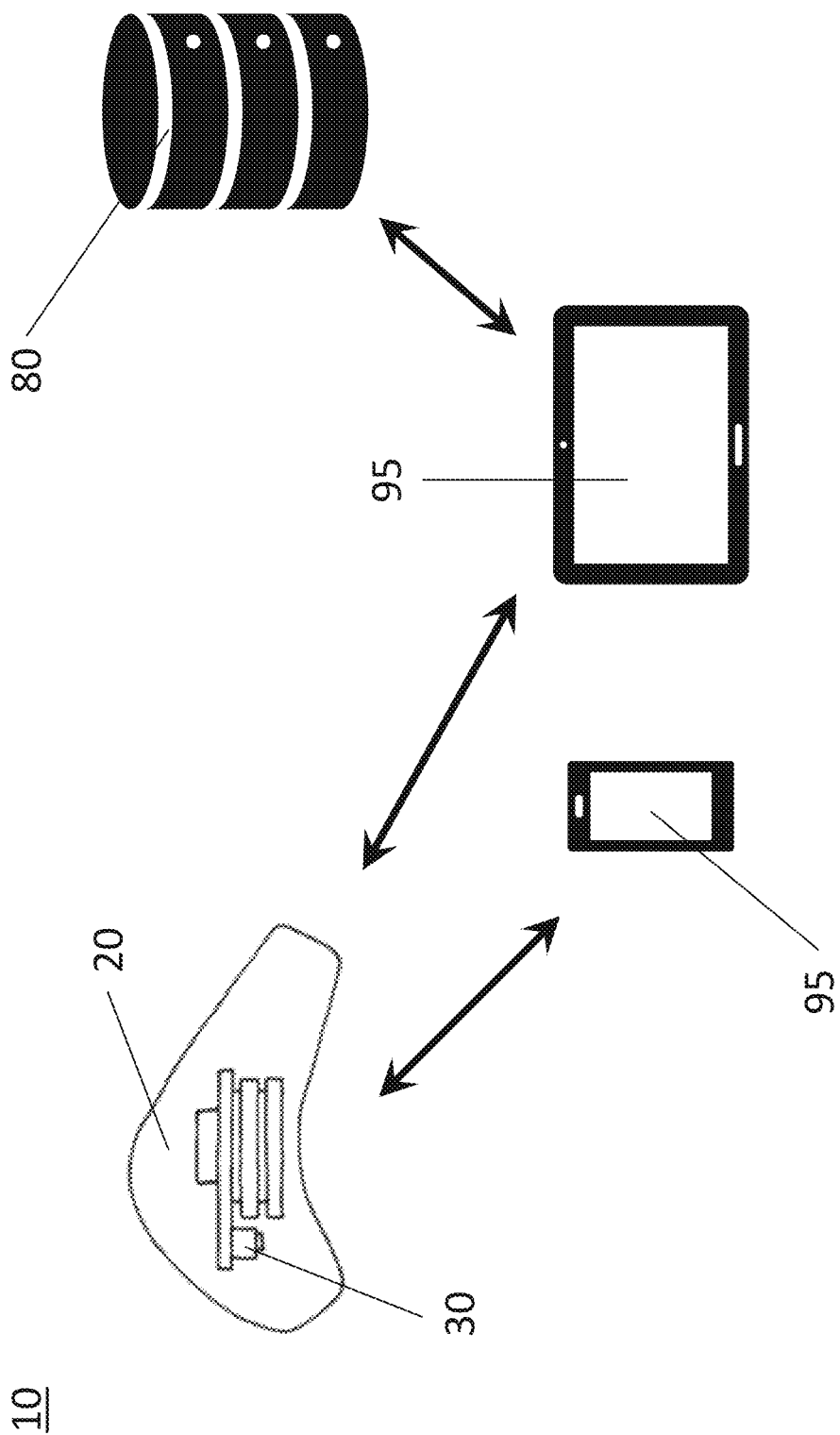
FIG. 5 illustrates an exemplary embodiment of a component level description of the system comprising the frequency transmitting device, a remote server, and a remote user device wherein the device communicates with a remote user device.
Figure 6:
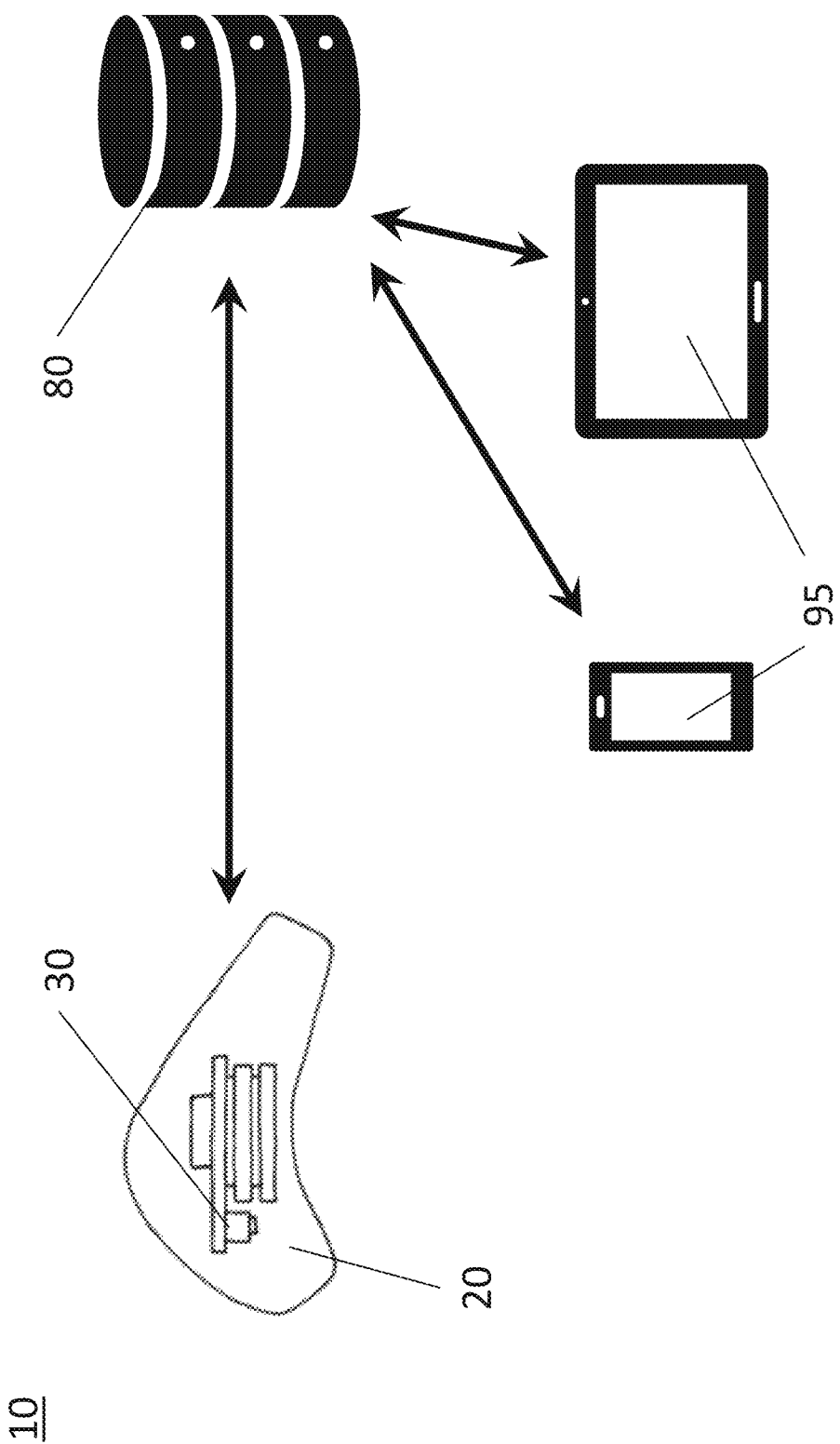
FIG. 6 illustrates an exemplary embodiment of a component level description of the system comprising the frequency transmitting device, a remote server, and a remote user device wherein the device communicates with a remote server.

As shown in FIGS. 5 and 6, the device 10 can transmit, or transmit and receive the recorded data through a variety of means. In one embodiment, the device 10 records the data and sends it to the user's phone, tablet or other remote device 95 via Bluetooth or similar communication technology. The data is then sent to a database 80 from the phone where it is stored for later access or analysis. As also shown in FIGS. 5 and 6, the user's phone, tablet or other device 95 can receive relevant data from the device 10, and/or sent relevant data to the device 10 through known two-way signal communication protocols, such as a Wi-Fi or Bluetooth protocols. The database 80 may also be communicatively connected with the user's phone to allow the user to view the trends and data in a user-friendly fashion. In further embodiments, the system 10 may be configured in other architectures with additional communication components that alternatively allow the data to be recorded and stored, and later displayed to the user.

Figure 7:
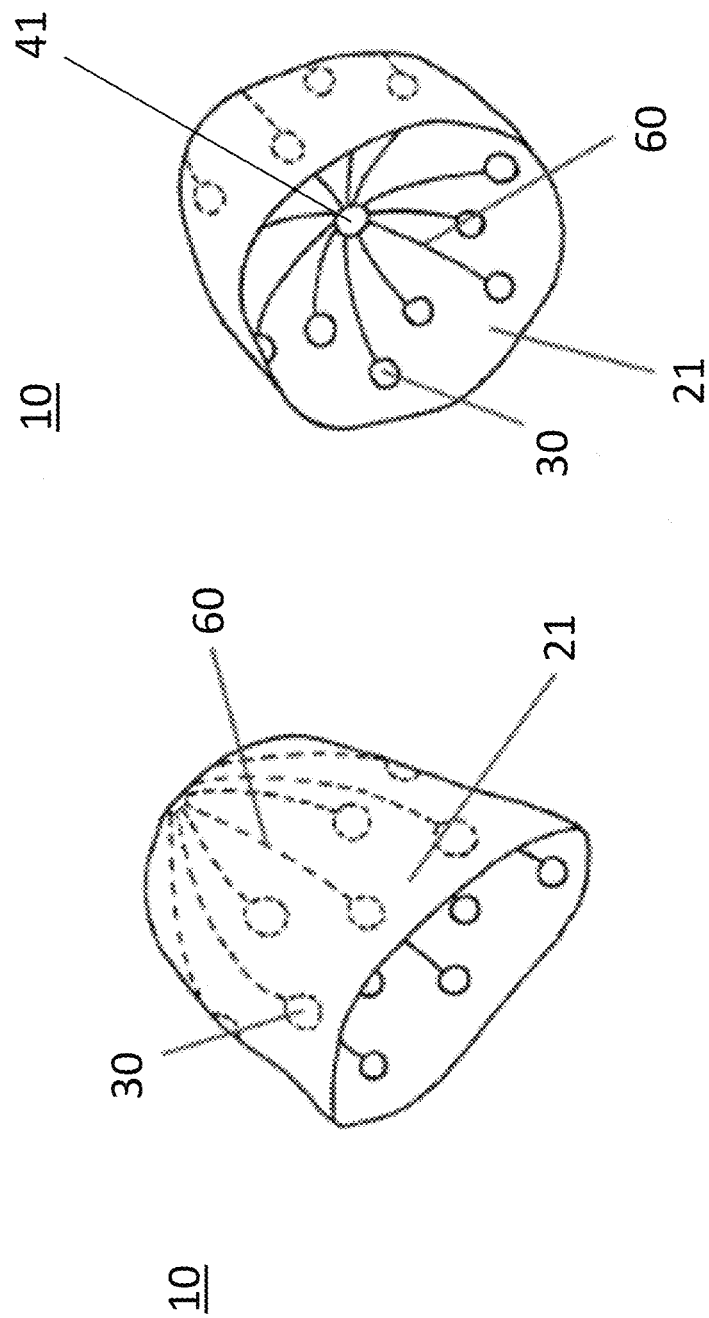
FIG. 7 shows an exemplary embodiment of the device in a hat/cap configuration with a system of stimulation nodes.

In a further embodiment of the inventive system, the frequency transmitted elements 30 may be implemented into any wearable apparel. In one such a configuration, as shown in FIG. 7, the system 10 is implemented into headwear 21. The stimulation nodes 30 are spread out throughout the apparel in a "spider web" fashion. In such configuration, the user is able to select which nodes/areas they want to emit the stimulation. The user is also able to choose if they want stimulation at one single frequency, or to have the stimulation at varying frequencies, intensities and patterns.

For example, a user could choose to have a "wave" or "sweeping" pattern of stimulation, standalone or in addition to other patterns. A user can also choose to have the stimulation constant, with or without specific isochronic tones. In this configuration, as shown in FIG. 7, there are flexible arms 60 that attach the nodes 30 to the system 10. These arms 60 are able to bend to fit the user's body comfortably and allow for the movement and positioning of any of the nodes 30. The device 10 can also be incorporated into any material or specific apparel. With this configuration, the user can wear the device to ensure ease of use and accessibility.

Figure 8:
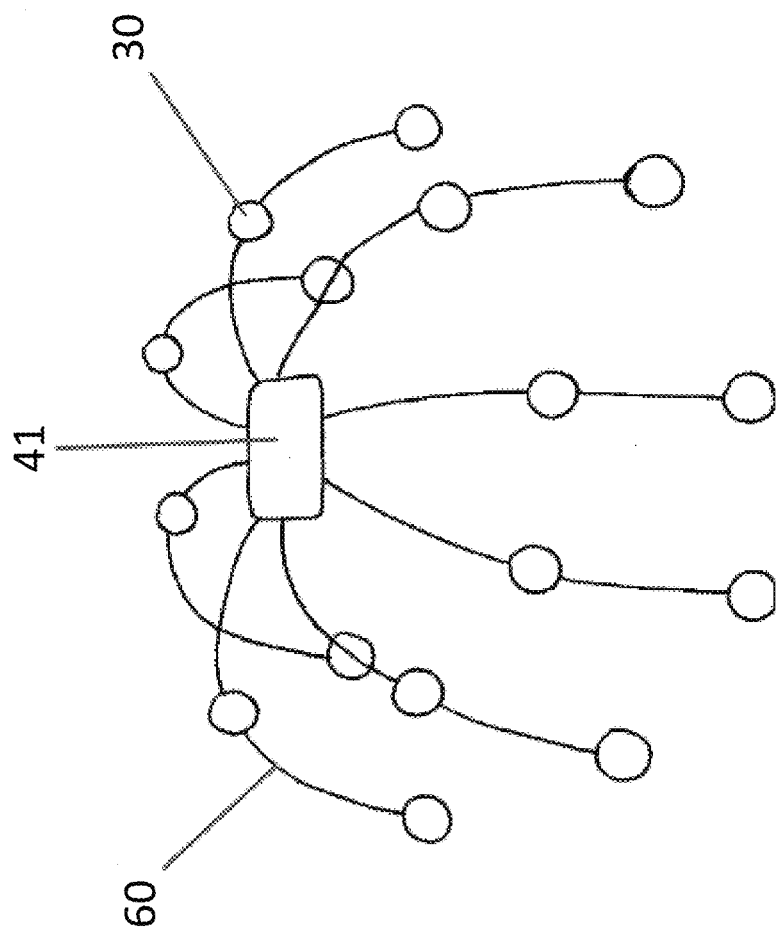
FIG. 8 shows an exemplary embodiment of the device in a configuration that combines a system of stimulation nodes.

Similar to the device configuration illustrated in FIG. 7, the "spider web" configuration of the system may also be worn without being incorporated into a hat or apparel. The configuration seen in FIG. 8 shows the device 10 in the webbed system which can be placed on a user's head. As described above, the user can manipulate the flexible arms 60 to choose where each stimulation node 30 is placed to have the greatest effect. The stimulation nodes 30 are capable of delivering a variety of emission signals. At the top of the device in this configuration, there is a small control panel 41 where the user can turn the device on and off, as well as manipulate one or more of the settings that have been previously described. As shown in FIG. 7, and described above, this configuration can be placed or integrated into any hat, headwear or any other apparel that a user desires.

Figure 9:
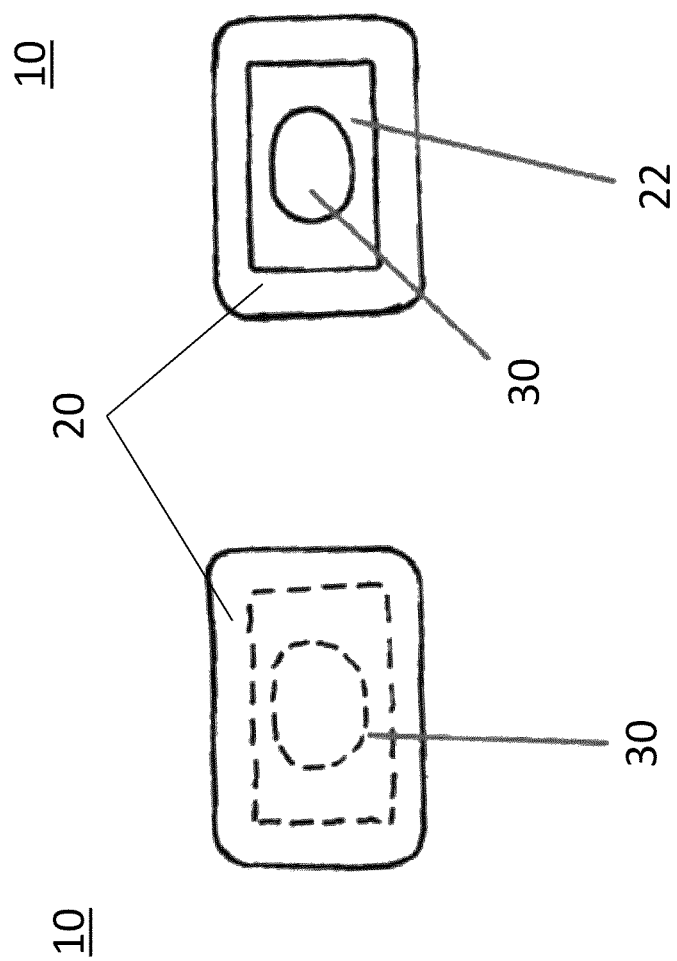
FIG. 9 shows an exemplary embodiment of the device using an adhesive configuration that can stick to the user's apparel or body.

As shown in FIG. 9, the device 10 includes an adhesive 22 such that the user can choose to place a node 30 either directly on their body, or in any apparel that the user may choose to wear. With this configuration, the user can be extremely specific about where they want to place the stimulation node 30, as well as how many nodes 30 that they would like to use.

The system can be programed to achieve different stimulation sequences throughout the nodal system such as sweeping pulses or constant stimulation in addition to various stimulation methods capable within the other configurations.

In this embodiment, adhesive material 22 is used to stick the respective nodes to any surface. As shown in FIG. 8, the system and device 10 will internally include a small printed circuit board 35, battery 40 and internal components necessary to operate the device 10, as well as at least one stimulation node 30. If a user wants to use more than one adhesive version of the device 10, they can sync each device 10 together so that the system operates in a unified fashion with all of the devices 10.

The device in different embodiments can also have electroencephalogram technology that will read the user's brainwaves. Based on these readings, the device can either send a notification to the user's phone when certain brainwave patterns are sensed or may automatically activate the device to subdue unwanted brain states preemptively. The device in certain embodiments can use a variety of embedded or internal sensors to measure various physiological metrics, including brainwaves, perspiration, respiration rate, and/or heart rate. Alternatively, the device 10 may use separate sensors to obtain one or more of various desired physiological metrics. Such separate sensors would necessarily be communicatively connected to device 10 to transmit the sensed physiological data.

With the adhesive configuration, the measurement technologies can be worn at all times and synched the system that communicates with the user's phone, tablet or other device to constantly monitor the user's metrics. All of this information will be incorporated into a user-friendly display.

Figure 10:
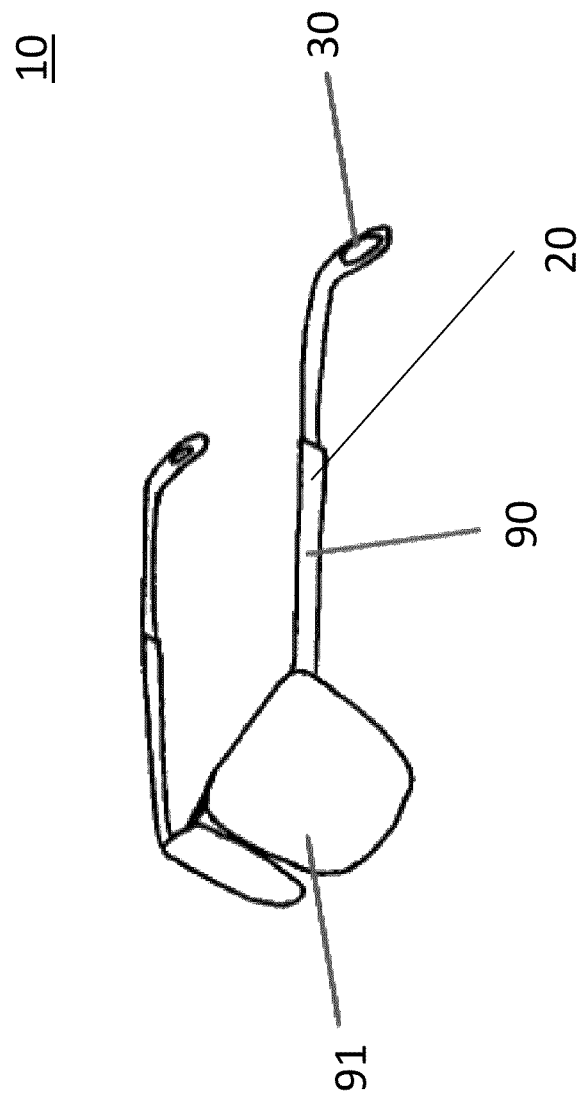
FIG. 10 shows an exemplary embodiment of the device in an eye-glasses configuration.

In still a further embodiment, as shown in FIG. 10, the device 10 can be incorporated into eyeglasses or sunglasses 90. In this configuration, there are stimulation nodes 30 in the distal end of each earpiece of the glasses 90. There may also be stimulation nodes 30 integrated around the lens rim 91 that can also transmit photic and other stimulation. The electronic components that operate the system may be integrated into frame of the glasses.

Figure 11:
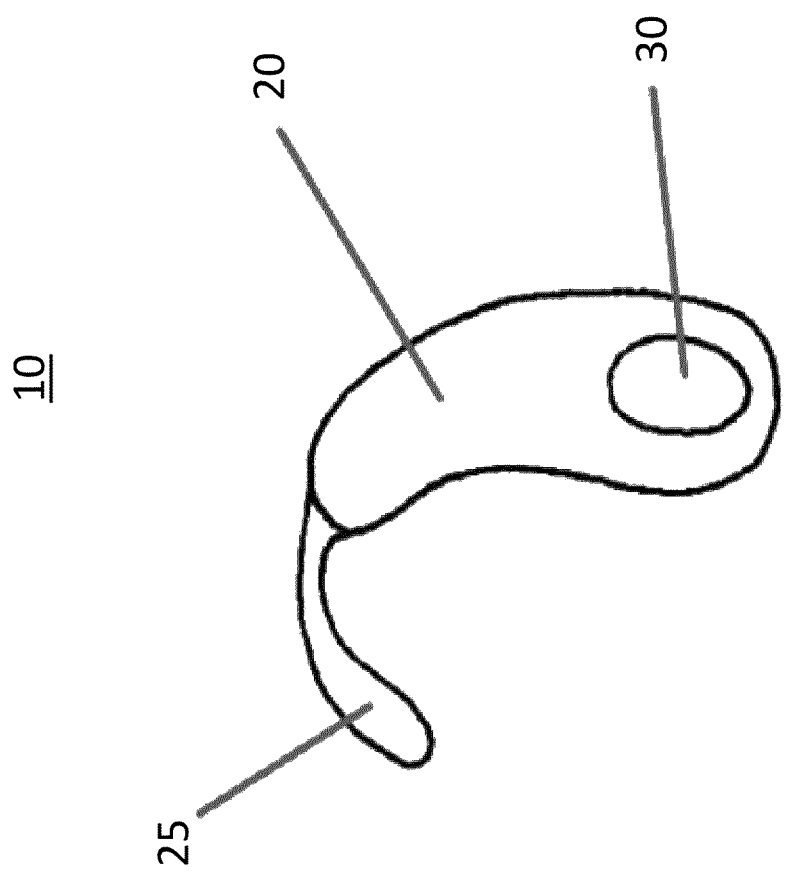
FIG. 11 shows an exemplary embodiment of the device in an over the ear configuration.

As shown in FIG. 11, the device 10 can also be configured into a wearable device that is worn over the ear, similar to a hearing aid. The simulation node 30 is integrated into the base of the device that fits behind the user's ear. The electronic components that operate the system are stored within the enclosed portion of the housing 20. In this configuration, there is a flexible arm 25 that allows the user to fasten the device 10 around his or her ear in a comfortably position, and still being securely placed.

Figure 12:
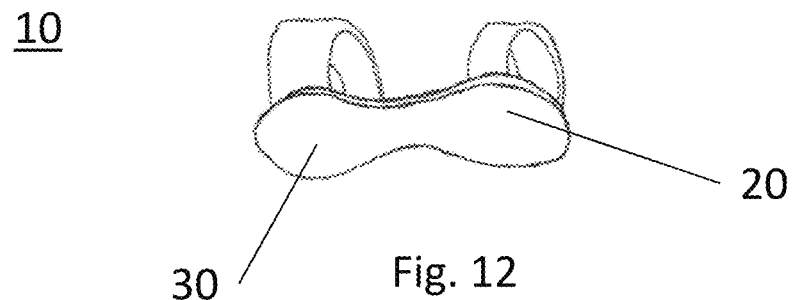
FIG. 12 shows an exemplary embodiment of the device attachable to a user's finger.
Figure 13:
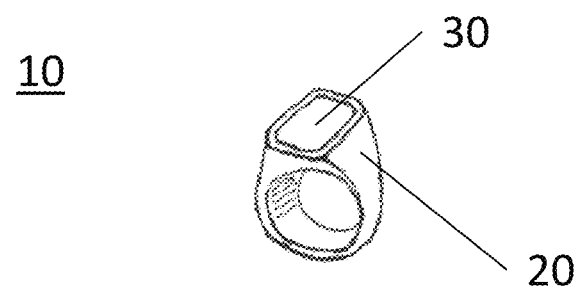
FIG. 13 shows an exemplary embodiment of the device in a configuration of a ring to be worn on a user's finger.
Figure 14:
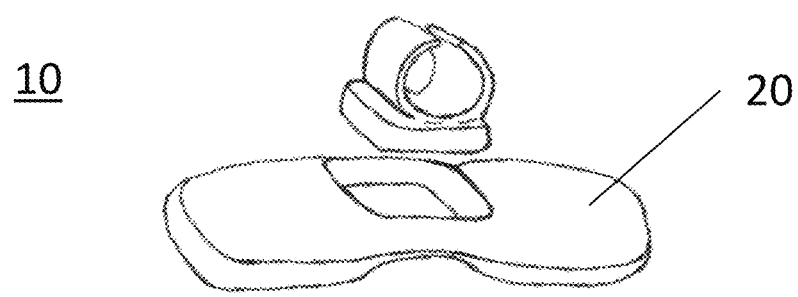
FIG. 14 shows an exemplary embodiment of the device similar to the FIG. 12 embodiment, with a detachable ring element.

In further embodiments and configurations, as shown in FIGS. 12 through 16, the device and system 10 may be fabricated into alternative sizes and configurations that are equally effective and operational. For example, as shown in FIGS. 12 and 13, the device may be very discreetly configured to be a ring or finger type device that the user can easily place on his or her finger, and then simply position his or her hand and the device 10 behind their ear. In a further variation, the embodiments illustrated in FIGS. 12 and 13 may be combined such that a single ring element may be formed to fit into a housing as shown in FIG. 14.

Figure 15:
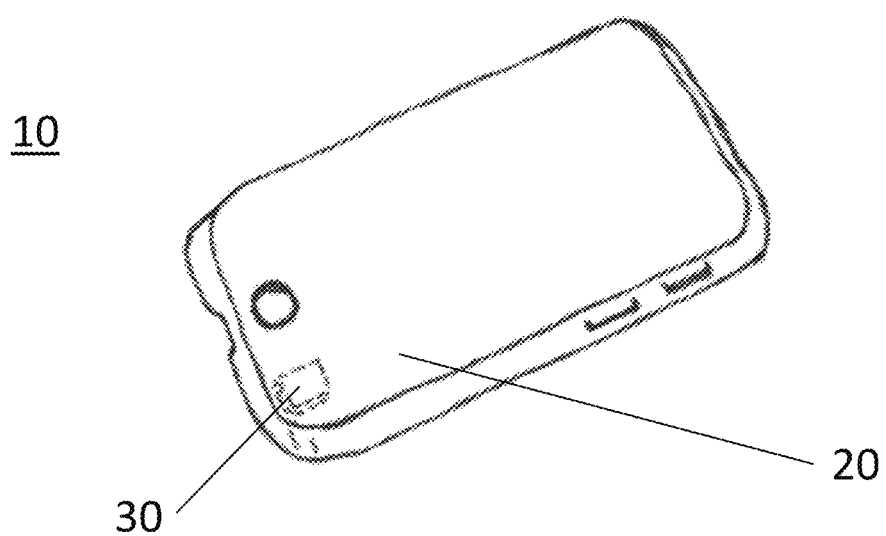
FIG. 15 shows an exemplary embodiment of the device implemented within a cover element for a smart phone.

Similarly, as shown in FIG. 15, the device 10 may be configured to be incorporated into a smartphone case, such that the smartphone case is the housing 20, and then allows a user to position and rest the smartphone case behind the user's ear. As an alternative to having a separate case with a frequency transmitting element 30, a software app may be downloaded to uses the shaker, vibration or haptic elements typically included in a smartphone, to generate the desired frequency signals. In this "app" configuration, the user can similarly position his or her smartphone behind his or her ear to impart the period frequency signal and thereby control any anxiety attacks.

As described, in various embodiments, the device 10 can produce various ranges of frequencies, amplitudes, tones, and pitches. Moreover, as illustrated and disclosed above, the device may be fabricated or configured into a wide variety of shapes, sizes, and configurations. A variety of interchangeable stimulation nodes/components can be utilized to impart the periodic frequency tones to the user. A variety of printed circuit board configurations can also be utilized to provide an effective means of imparting the intended wave forms. The device is compact and discreet to allow the individual to achieve desired brainwave synchronization.

In various embodiments, the device and system also incorporate bio-feedback and electroencephalogram capabilities. More particularly, in such embodiments there is a transmitter/receiver component 38 in the device 10 that records when the device 10 is on and operating, as well as the duration of use of the device 10. The recorded data is then transmitted to a separate database. The individual using the device is then able to use their smartphone, tablet, or visit a website to view trends and patterns regarding their device's usage.

When utilizing the application and with the device 10 being in an on state, the application pushes a notification to the user's phone (or whichever device is synched with the anxiolytic device) and asks the user if they are experiencing or had an anxiety attack. The user is then able to record, if known, why the attack occurred, and record notes that may be relevant or important to the attack. The data is stored and displayed in a user-friendly format to show how frequently an individual is having attacks/stress as well as in what environments such conditions are manifested. With such data and analytics, the user may be able to recognize certain trends and then use this information to help prevent further anxiety attacks/stress.

Clinical professionals such as psychologists and psychiatrists, as well as parents, caretakers and other authorized recipients may also be able to download the application to view the user's data. Clinical professionals or caretakers can then review the data to determine any trends or other valuable data to gain a better insight on the user's condition, and then may be able to structure more personalized treatment, coping methods, and focused therapy sessions. All of this data will be recorded and sent through the transmitter/receiver component 38 in the device 10.

In addition to addressing anxiety and stress levels, the device has the capability to combat many different non-desired conditions, discomfort levels, or non-desired states of mind.

Figure 16:
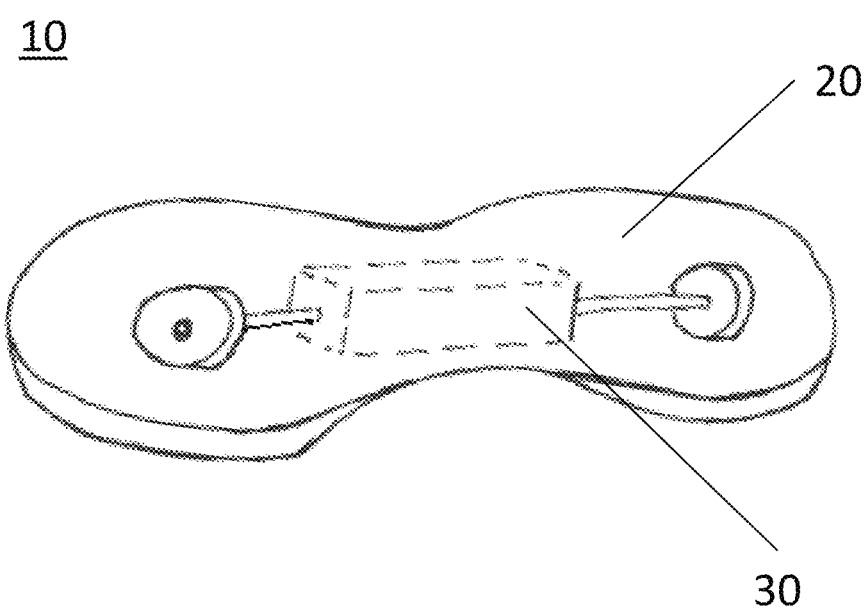
FIG. 16 shows an exemplary embodiment of the device using a translating element of a solenoid to provide the frequency or vibratory signal.

While several preferred embodiments and features of the inventive devices and systems for proactively influencing brainwave states have been described and disclosed, in particular with reference to the attached figures and drawings showing certain exemplary embodiments that relate to a particular embodiments and system components, such exemplary embodiments as shown are not to be construed as limiting the scope of the inventive device or systems. More particularly, as exemplified by the above described embodiments, alternative embodiments and configurations may be created that allow the user to discreetly use the device to impart a form of periodic frequency stimulation to influence the user's brainwave state to achieve a non-anxiety, non-elevated stress level condition. Moreover, alternative means of providing the frequency transmitting signal to the user may be incorporated into the device. While certain forms of frequency transmitting elements 30 have been disclosed and shown, alternative elements, such as a solenoid, as illustrated in FIG. 16, may be equally effective for operation and use.

It will be recognized by those skilled in the art that other modifications, substitutions, and/or other applications are possible and such modifications, substitutions, and applications are within the true scope and spirit of the present invention. It is likewise understood that the attached claims are intended to cover all such modifications, substitutions, and/or applications.

What is claimed is:

1. A device for influencing brainwaves and brain states, comprising:
   a. a housing conformably placeable upon an outer surface of an individual's skull;
   b. at least one frequency transmitting element housed within said housing;
   c. a switch to actuate said at least one frequency transmitting element;
   d. a power source housed within said housing;
   e. a computer processor housed within said housing;
   f. read only memory (ROM) coupled to said computer processor to store at least one .wav files; and
   g. at least one wave form data file stored within said ROM as a .wav file;

wherein when said switch is actuated, said computer processor is configured to read said at least one wave form data file stored as a .wav file in said ROM, and then drive said at least one frequency transmitting element to match said at least one wave form data file, imparting a signal to the individual's skull that matches characteristics of said at least one wave form data file.

2. The device for influencing brainwaves and brain states, as described in claim 1, wherein said at least one wave form data file is an isochronic wave pattern.

3. The device for influencing brainwaves and brain states, as described in claim 1, wherein said at least one wave form data file includes a plurality of frequencies and amplitudes.

4. The device for influencing brainwaves and brain states, as described in claim 1, wherein said housing is incorporated into a hearing aid device that is configured to fit about a user's outer ear.

5. The device for influencing brainwaves and brain states, as described in claim 1, wherein said device is incorporated into wearable apparel.

6. The device for influencing brainwaves and brain states, as described in claim 1, wherein said at least one frequency transmitting element is driven at varying frequencies matching a plurality of frequencies of said at least one wave form data file.

7. The device for influencing brainwaves and brain states, as described in claim 1, wherein said power source is at least one rechargeable battery.

8. A system for influencing brainwaves and brain states, comprising:
   a. a housing conformably placeable upon an outer surface of an individual's skull;
   b. at least one frequency transmitting element housed within said housing;
   c. a switch to actuate said at least one frequency transmitting element, said switch located within said housing;
   d. a rechargeable power source housed within said housing;
   e. a computer processor housed within said housing;
   f. read only memory (ROM) coupled with said computer processor to store a plurality of .wav files; and
   g. a plurality of wave form data files stored within said ROM as .wav files;
   h. at least one sensor to record at least one physiological metric of a user;
   i. a data transmitter incorporated into said housing to transmit data received from said at least one sensor; and
   j. at least one remote device to receive data transmitted from said data transmitter;

wherein when said switch is actuated, said computer processor is configured to read said wave form data files stored as .wav files in said ROM, and drive said at least one frequency transmitting element at a frequency matching at least one frequency of said wave form data files, whereby said frequency transmitting element imparts said at least one frequency to the outer surface of the individual's skull.

9. The system for influencing brainwaves and brain states, as described in claim 8, wherein said at least one sensor is an electroencephalogram sensor.

10. The system for influencing brainwaves and brain states, as described in claim 8, wherein said wave form data files are an isochronic wave pattern.

11. The system for influencing brainwaves and brain states, as described in claim 8, wherein said wave form data files include a plurality of frequencies.

12. The system for influencing brainwaves and brain states, as described in claim 8, wherein said housing is incorporated into a hearing aid device that is configured to fit about a user's outer ear.

13. The system for influencing brainwaves and brain states, as described in claim 8, wherein said housing is incorporated into wearable apparel.

14. The system for influencing brainwaves and brain states, as described in claim 8, wherein said rechargeable power source is at least one rechargeable battery.

\* \* \* \* \*